(12) United States Patent
Clark et al.

(10) Patent No.: US 11,412,958 B2
(45) Date of Patent: Aug. 16, 2022

(54) SYSTEMS AND METHODS FOR USER-DEPENDENT CONDITIONING OF STIMULI IN TESTS USING A METHOD OF CONTINUOUS ADJUSTMENT

(71) Applicant: Mimi Hearing Technologies GmbH, Berlin (DE)

(72) Inventors: Nicholas R. Clark, Royston (GB); Vinzenz H. Schönfelder, Berlin (DE); Tina Baumann, Berlin (DE)

(73) Assignee: Mimi Hearing Technologies GmbH, Berlin (DE)

( * ) Notice: Subject to any disclaimer, the term of this patent is extended or adjusted under 35 U.S.C. 154(b) by 466 days.

(21) Appl. No.: 16/355,449

(22) Filed: Mar. 15, 2019

(65) Prior Publication Data

US 2019/0209054 A1 Jul. 11, 2019

Related U.S. Application Data

(63) Continuation-in-part of application No. PCT/EP2018/057339, filed on Mar. 22, 2018.

(30) Foreign Application Priority Data

Mar. 22, 2017 (EP) .................................... 17162448
May 16, 2017 (EP) .................................... 17171413
Mar. 22, 2018 (GB) .................................... 1804604

(51) Int. Cl.
*A61B 5/12* (2006.01)
*A61B 5/16* (2006.01)
*A61B 5/00* (2006.01)
*G06F 3/01* (2006.01)

(52) U.S. Cl.
CPC .............. *A61B 5/121* (2013.01); *A61B 5/123* (2013.01); *A61B 5/16* (2013.01); *A61B 5/486* (2013.01);
(Continued)

(58) Field of Classification Search
CPC ......... A61B 5/121; A61B 5/486; A61B 5/123; A61B 5/7475; A61B 5/16; A61B 5/7225; G06F 3/015
See application file for complete search history.

(56) References Cited

U.S. PATENT DOCUMENTS 3,673,328 A * 6/1972 Grason .................... A61B 5/12
73/585

FOREIGN PATENT DOCUMENTS

EP 1796355 A2 6/2007
EP 2572640 A1 3/2013

OTHER PUBLICATIONS

Sęk et al. (2007). A fast method for the determination of psychophysical tuning curves: Further refining. Archives of Acoustics. 32. 707-728. (Year: 2007).*

(Continued)

*Primary Examiner* — Devin B Henson
*Assistant Examiner* — Justin Xu
(74) *Attorney, Agent, or Firm* — Polsinelli PC

(57) ABSTRACT

Disclosed are systems and methods for user-dependent conditioning of stimuli in tests to elicit user responses to variations of one or more adaptive parameters of a user stimulus signal. The user stimulus signal is generated based on first and second adaptive parameters. The first adaptive parameter is modified to thereby generate a plurality of successive variations in the user stimulus signal, over one or more ranges of values of the second adaptive parameter. In response to modifying the first adaptive parameter, a plurality of user responses from a given user are received. Each user response indicates that one of the plurality of successive variations in the user stimulus signal has occurred. Based on an expected user response curve for the given user and a calculated time interval between successive user responses, an instantaneous rate of change for modifying the first (Continued)

adaptive parameter is adjusted such that the user responses are steered toward a neutral state around the expected user response curve.

20 Claims, 4 Drawing Sheets

(52) U.S. Cl.
CPC .......... *A61B 5/7225* (2013.01); *A61B 5/7475* (2013.01); *G06F 3/015* (2013.01)

(56) References Cited

OTHER PUBLICATIONS

Sę k et al. (2007). A fast method for the determination of psycho-physical tuning curves: Further refining. Archives of Acoustics. 32. 707-728. (Year: 2007).*
Leek, Marjorie. (2001). Adaptive procedures in psychophysical research. Perception and Psychophysics. 63(8), 1279-1292. (Year: 2001).*
Grant, Ruth, W.; "Strings Attached"; Nov. 18, 2016; Retrieved from the Internet: https://web.archive.org/web/20151116011353/http://www.myfitnesspal.com/welcome/learn_more; Princeton; pp. 3.
International Searching Authority; "International Search Report & Written Opinion"; dated May 2, 2018; From corresponding PCT application PCT/EP2018/057339; pp. 17.
GB Intellectual Property Office; "Search Report under Section 17"; dated Sep. 17, 2018; From corresponding GB application GB1804604.5; pp. 4.

* cited by examiner

SYSTEMS AND METHODS FOR USER-DEPENDENT CONDITIONING OF STIMULI IN TESTS USING A METHOD OF CONTINUOUS ADJUSTMENT

CROSS-REFERENCE TO RELATED APPLICATIONS

This application is a continuation-in-part of International Application Number PCT/EP2018/057339, filed Mar. 22, 2018 and entitled "METHODS FOR USER-DEPENDENT CONDITIONING OF STIMULI IN TESTS USING A METHOD OF CONTINUOUS ADJUSTMENT", the disclosure of which is herein incorporated by reference in its entirety.

FIELD OF INVENTION

The disclosure relates generally to the field of digital signal processing (DSP), audio engineering and audiology, and more specifically pertains to systems and methods for continuous adaptation based on user perception of and response to stimulus.

BACKGROUND

Various behavioral methods have been developed in psychophysics to obtain psychometric data from observers, e.g., to measure a person's hearing ability. For example, conventional methods include the method of limits, the method of constant stimuli, the method of adjustment, as well as forced choice methods. In the context of measuring an observer's hearing threshold, Bekesy developed a method of "continuous adjustment" called "Bekesy tracking" [Bekesy, G. v., *A new audiometer*, Acta Oto-Laryngologica, 35, 41, 1-422. (1947)]. By way of a simple binary interaction of the user (pressing or releasing a single button), a parameter, i.e. the amplitude, of a sound stimulus is constantly increased or decreased resulting in an oscillation around a threshold. The threshold level can then be estimated from the points of user interaction occurring above and below the threshold.

A "sweeping" Bekesy tracking paradigm represents a variant of that general method, where a second parameter of the stimulus (e.g. frequency) is constantly changed so that the level of the perceptual threshold is traced along a range of values of that parameter of the stimulus.

Originally developed for estimating pure tone auditory thresholds, the general mechanics of the Bekesy method, i.e. the continuous adjustment of parameters of a stimulus based on user interaction, have also been applied in other contexts, e.g. for estimating psychophysical tuning curves (PTC). [Sek, A., Alcantara, J., Moore, B. C. J., Kluk, K., & Wicher, A., *Development of a fast method for determining psychophysical tuning curves*, International Journal of Audiology, 44(7), 408-420. (2005)]. Bekesy audiometry has been recognized as a useful diagnostic tool in clinical audiology [see, e.g., Granitz, D. W. "An evaluation of diagnostic parameters of Bekesy audiometry", LSU Historical Dissertation Theses 2052 (1971)].

In a Bekesy tracking/continuous adjustment paradigm, for example, a user is tasked with pressing a button when he hears a sound and releasing the button when he does not. As long as the button is pressed, the parameter, i.e. the amplitude, of the stimulus is continuously reduced at a fixed rate until the user releases the button. When the button is released, the parameter, i.e. the amplitude, of the stimulus is increased at the same rate. As a result of this procedure, the parameter of the stimulus should continuously oscillate around the threshold level of a user at a given frequency.

Owing to its intuitive and engaging character, this method of continuous user-controlled adjustment of the parameter of the stimulus lends itself particularly well for (but is not limited to) consumer (e.g. mobile device) implementations of psychometric tests, such as audiometric hearing tests. Users can quickly learn the task and are not required to directly look at the device during a test, such that the user's continuous engagement allows for a large body of data to be collected over a relatively short period of time. The conventional implementation of such a continuous user-controlled adjustment paradigm uses equal upward and downward rates of change of the user-controlled parameter of a stimulus. Consequently, a "neutral" user interaction, i.e. pressing and releasing regularly and at uniform intervals, results in a flat (constant level) threshold estimate.

Generally, accuracy and reliability of the data in such a continuous adjustment paradigm is dependent on regularly occurring user interaction, i.e. a threshold can only be reliably estimated in a parameter region where the user gives regular feedback. If the actual threshold curve deviates significantly from the threshold levels that would be determined by "neutral" user interaction, users may only interact with the test very rarely. In addition, data may exhibit an unpredictable bias when users become confused or disoriented after not interacting with the test for longer periods of time.

The stimulus signal levels that a user can follow in a sweeping continuous adjustment paradigm, i.e. a paradigm wherein a second parameter is continuously varied as the user's response to the stimulus signal levels is measured, may be technically limited by the fixed rates of change of the stimulus level and the rate of change of the second, sweeping stimulus parameter. In particular, if the slope of the actual threshold curve is similar to, or steeper than this technical limit, the measured trace may not reflect the true thresholds beyond this limit.

Accordingly, it is an aspect of the present disclosure to provide systems and methods for obtaining a "neutral" response trace from the user such that the neutral response trace follows a shape that is closer to the actual threshold curve of the user. Advantageously, the user will provide more regular feedback, leading to more reliable data and less biased data. Such data can also allow for steeper threshold changes to be followed.

SUMMARY OF THE INVENTION

According to aspects of the present disclosure, provided are systems and methods that include a modification to a continuous adjustment paradigm in order to thereby facilitate "neutral" response behavior from a user. In some embodiments, the systems and methods include steps consisting of: estimating an initial expected response curve for a test of at least one parameter of a stimulus for a particular user, based on prior data and knowledge about that user; adjusting the rate of change of the or each parameter of the stimulus in response to the regularity of user interactions during the test in order to steer the user responses towards the expected response curve to obtain more uniform intervals between successive user interactions ("neutral" user interaction); and modifying the initial expected response curve in accordance with the test results when substantially neutral user interactions are not obtained across the test range for a selected parameter of the stimulus.

Neutral user interaction can be achieved by employing dissimilar rates of change of a stimulus parameter when increasing and decreasing the parameter level to which the user responds during the test, and/or by modifying the rate of change of this parameter depending on whether it is increasing or decreasing. In a sweeping auditory test, for example, this may mean adjusting separately for upward and downward sections of the sweeping auditory test, e.g. having faster rates of change in stimulus levels during level increases and slower rates of change in stimulus levels during level decreases. The performance of separate adjustments can steer the user response curve towards the expected response curve for the test parameter. As a result, any non-neutral behaviors of the user (test interaction at non-uniform intervals) will correspond to deviations of the actual trace from the initially predicted trace, and the predicted response contour can then be revised accordingly.

Aspects of the present disclosure thereby permit a continuous analysis of how well measured user response(s) match an initially expected response contour. By analyzing the actual and predicted user responses, the expected response curve can be continually adjusted in order to maximize the probability of obtaining an optimum data set for the user. In some embodiments, this may be achieved by a real-time windowed regression function calculation or LMS (least mean square) analysis of the user's responses against a dictionary, and/or may be achieved by utilizing a parametric model of actual responses from previous tests (of the same or other users) to dynamically adapt the expected response contour during the test.

A method of the present disclosure may include further modifying the expected response curve in accordance with detected test results when substantially neutral user interaction is not obtained across the range of variation of the second variable parameter. The second variable parameter of the stimulus may be continuously varied monotonically across the range of values for the test. The actual and expected user responses and the degree of neutral user interaction may be continuously analyzed and monitored, and the expected response curve may therefore be continually adjusted to maximize the probability of obtaining neutral user interaction across the range of values for the test.

In some embodiments, the rate of change of increases in the adaptive parameter of the stimulus to meet the specified condition may be increased when one or more expected response curves predict that the specified condition will not be met, and neutral interaction will not be obtained without such increase.

In some embodiments, the rate of change of decreases in the adaptive parameter of the stimulus after the specified condition has been met may be decreased when one or more expected response curves predict that the specified condition will not cease to be met (i.e. will continue to be met), and neutral interaction will not be obtained without such decrease.

In some embodiments, systems and methods according to aspects of the present disclosure can be used for an audiometric test, wherein the test comprises one or more of a supra-threshold test, a psychometric tuning curve test, a masked threshold test, a temporal fine structure test, or a temporal masking curve test. In particular, the supra-threshold test may be a psychometric tuning curve test or a masked threshold (MT) test. In some embodiments, the psychometric tuning curve test may be measured for signal tones between frequencies of 500 Hz and 4 kHz and at a sound level of between 20 dB SL and 40 dB SL, in the presence of a masking signal for the signal tone that sweeps from 50% of the signal tone frequency to 150% of the signal tone frequency. In some embodiments, the MT test (a similar, albeit inverted paradigm to the PTC test) may be measured for a narrow band of noise between center frequencies of 500 Hz and 4 kHz while a probe tone sweeps from 50% of the noise band center frequency to 150% of the noise band frequency.

In some embodiments, the adaptive parameter of the stimulus may be an audio signal amplitude. The second variable parameter of the stimulus may be an audio tone frequency.

In some embodiments, the rate of change of the second variable parameter of the stimulus may also be varied to steer the user responses towards neutral user interaction around the expected response curve with more uniform intervals between successive user interactions.

In some embodiments, a method according to aspects of the present disclosure can be implemented under control of a software application for use on a non-calibrated or unreferenced audio system and adapted for a user to self-administer the test.

In some embodiments, aspects of the present disclosure include systems and methods for user-dependent conditioning of stimuli in a test to elicit user responses to variations of an adaptive parameter of a stimulus utilizing a method of continuous adjustment to obtain a response curve indicative of the user's perception of the variations in the adaptive parameter of the stimulus over a range of values of a second variable parameter of the stimulus; the user responses comprising binary indications of whether or not the varying adaptive parameter of the stimulus meets a specified condition as the second variable parameter of the stimulus is also varied; each change of binary indication being identified as a user interaction, the method being directed to obtain at least a predetermined number of user interactions around the response curve. The systems and methods can include steps consisting of: estimating the expected response curve for the user based on prior data and knowledge about the test and the user; and adjusting the rate of change of the adaptive parameter of the stimulus depending on the regularity of user interactions during the test, the adjustments being directed to obtain at least a predetermined number of user interactions over the range of values of the second variable parameter of the stimulus.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which.

DETAILED DESCRIPTION

Various example embodiments of the present disclosure are discussed in detail below. While specific implementations are discussed, these implementations are for illustration purposes only. One of ordinary skill in the art will recognize that other components and configurations may be used without parting from the spirit and scope of the disclosure.

Disclosed are systems and methods for user-dependent conditioning of stimuli in tests to elicit user responses to variations of an adaptive parameter of a stimulus. By continuously adjusting the stimulus to obtain a response curve indicative of the user's perception of the variations in the adaptive parameter of the stimulus, aspects of the present disclosure maximize regularity of user interactions around the response curve. Such improvements are particular desirable in audiometric tests, including when such audiometric tests are carried out using unreferenced or non-calibrated audio systems. Although the forthcoming discussion focuses on an exemplary such unreferenced or non-calibrated audio system, the example is for purposes of illustration and is not intended to be construed as limiting. It is appreciated that aspects of the present disclosure can further be applied in and used for similar test applications in other fields of sensory behavioral science, e.g. where a user interaction is measured in response to stimulus adaptations. In some embodiments, systems and methods of the present disclosure can include a computer program or mobile application on a user computing device, thereby allowing one or more user computing devices to be used as a non-calibrated audio system for the user to perform self-administered tests.

The systems and methods according to aspects of the present disclosure address the problems of improving the efficiency and utility of tests, for example hearing tests, performed under uncertain conditions. The systems and methods in particular involve making predictions of an expected test response curve, contour or profile for a user, based on prior data and knowledge about the user. The prior data may comprise information on the user's responses in previous tests, and/or comparative information on test results from a database of other users with similar socio-demographic profiles and pathology. Based on the predictions, continuous real-time adjustments of one or more test parameters are made in substantially real-time, i.e. during a test, in order to thereby steer user responses towards a predicted or expected response contour of the user, thus maximizing user response symmetry around an adaptive parameter of a stimulus.

Figure 1:
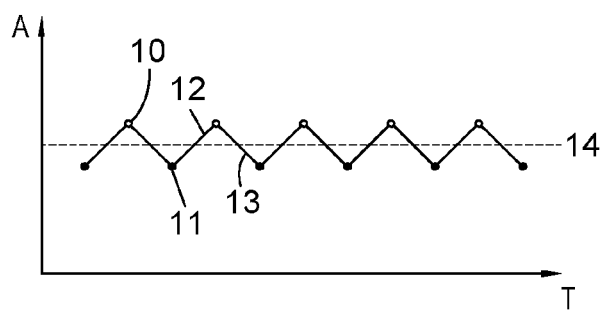
FIG. 1 illustrates user interactions in response to a Bekesy tracking method of continuous adjustment of a stimulus level at steady rates up and down over time.

The disclosure now turns to FIG. 1, which illustrates discrete user responses 10,11 that are associated with changes in a stimulus level A (shown on the vertical axis) of a single adaptive parameter vs. time T (shown on the horizontal axis). For example, a single adaptive parameter might correspond to an audio signal amplitude or level at a specific pure tone frequency, although it is appreciated that various other adaptive parameters can be utilized without departing from the scope of the present disclosure.

The user responses 10,11 are collected at discrete points in time. For example, user response 10 is measured when a user presses and holds a button when the user determines that the audio tone of the hearing test reaches an audible level. User response 11 is measured when the user releases the button, i.e. once the user determines that the audio tone of the hearing test is no longer audible (i.e. reaches an inaudible level).

Between the released and pressed button states of user responses 10,11, the tone amplitude of the audio test is varied at one or more constant rates. In some embodiments, one or more of the constant rates can be calculated in accordance with a Bekesy tracking paradigm. Thus, when the button is released at user response 11, the stimulus level of the audio tone is then increased at a constant rate 12 until the user once again presses and holds the button in response to being able to hear the audio tone of the hearing test. The stimulus level of the audio tone is then decreased at a constant rate 13 until the user is no longer able to hear the audio tone and releases the button. The cycle then repeats as described above (although potentially with varying rates of increase/decrease in audio tone stimulus level) until the hearing test is terminated or otherwise concluded.

As can be seen in FIG. 1, the user response pairs (such as user response pair 10,11) thereby oscillate consistently around a threshold level 14.

Figure 2:
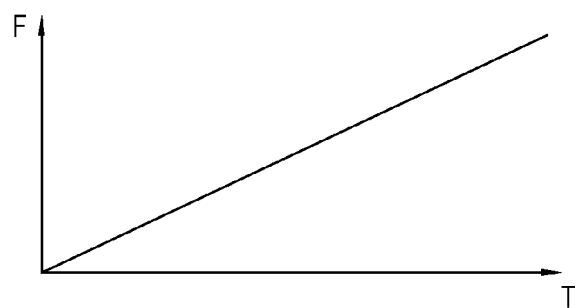
FIG. 2 illustrates change of a second stimulus parameter over time, consistent with a "sweeping" Bekesy tracking paradigm.

FIG. 2 illustrates the change of a second stimulus parameter over time, in a sweeping Bekesy paradigm. In particular, the second independent stimulus parameter in this case is frequency F, continuously varied over time T. During the hearing test, the user thus responds to changes in the first stimulus level as the second stimulus level is also changed.

Figure 3:
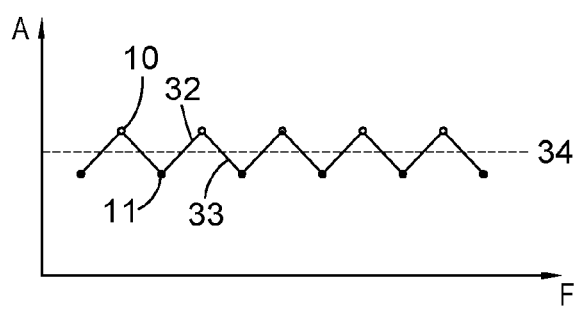
FIG. 3 illustrates "neutral" user interactions in response to changes in stimulus levels and frequency over a test frequency range.

FIG. 3 illustrates an example of what is referred to herein as "neutral" user interaction, where the user responses of pressing (i.e. user response 10) and releasing a button (i.e. user response 11) are measured at regular intervals. In this case, the first stimulus level (i.e. audio signal amplitude A) is varied up and down as the second stimulus parameter (i.e. audio tone frequency F) is continuously oscillated between lower and higher levels. The threshold level associated with this hearing test is thus also measured across a range of values of the second parameter (frequency F), thereby following a sweeping Bekesy tracking paradigm.

As in the standard Bekesy tracking paradigm, the stimulus level of the first parameter (i.e., the stimulus level of the audio tone) is increased at a constant rate 32 when the button is released and is decreased at a constant rate 33 when the button is pressed. Throughout this variation of the first parameter, the second parameter (frequency F) is monotonically increased. This results in a threshold curve 34 that is calculated over a range of frequencies, rather than the single threshold level for a single frequency tone such as the one shown in FIG. 1. The user's interaction is "neutral" in this example (i.e. substantially the same as threshold curve 14 of FIG. 1), because the threshold curve 34 in fact happens to be at a constant level across this limited frequency range. This will not be so across the whole of an individual's normal hearing range.

Figure 4:
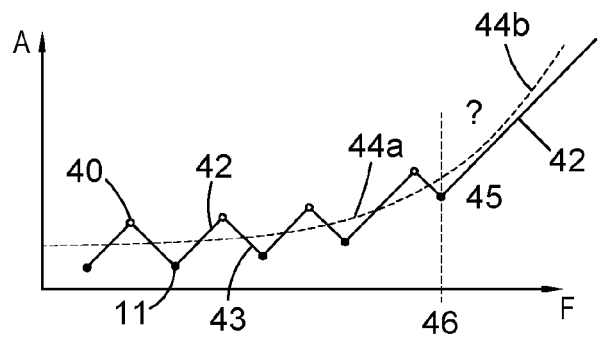
FIG. 4 illustrates the problem whereby variations in a user's sensitivity to changes in the adaptive parameters under a conventional sweeping Bekesy paradigm lead to a loss of interaction.

FIG. 4 illustrates on such example situation which arises when a user's response curve to changes in the first parameter (audio tone level) of a stimulus is not constant with respect to changes in the second parameter (audio tone frequency) of the stimulus. For example, this can occur when a user's audio threshold levels vary significantly at or between higher and/or lower frequencies. Thus, when the threshold curve 44 deviates significantly from a substantially constant level, the user interactions of pressing 10, and releasing 11, the button become less regular and less frequent. Eventually, after a final button release 45, the user no longer interacts with the audio test. In these circumstances, whilst response data allows reliable validation of the expected response curve 44a below a cut-off frequency 46, no data is obtainable to validate the response curve 44b above the cut-off frequency 46. The reason for this lack of data lies in the fixed rates of increase 42 and decrease 43 of the stimulus level (i.e. the audio tone level). After the last user interaction 45 with the button, the fixed rate of change of increase 42 in the stimulus level with change in the frequency is actually less than the increase in the user's actual audio threshold level above the cut-off frequency 46. Thus, it is no longer possible to get any further user interaction, data, or measurement using the standard Bekesy paradigm.

Figure 5:
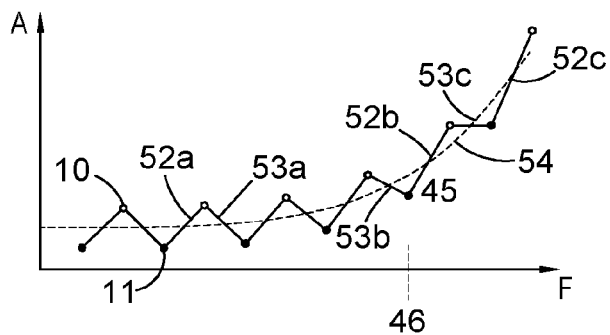
FIG. 5 illustrates how a modified continuous adjustment method according to the invention results in extended user interaction.

FIG. 5 illustrates an aspect of the present disclosure that solves this problem and extends the range of user interaction to obtain appropriate data beyond the cut-off frequency 46 by using a modified Bekesy paradigm. In this example, the increases and decreases in the stimulus level are not necessarily kept constant throughout (as in the standard Bekesy paradigm illustrated in FIG. 4), but are themselves adaptive and variable in real-time, according to one or more predicted and/or detected variations in rate of change of a user's threshold response curve 54 for the measured parameter. Accordingly, the audio tone stimulus level increases 52a,b,c are each associated with a successively larger rate of change, with 52a being the relatively smallest rate of change and 52c being the relatively largest rate of change. Similarly, the audio tone stimulus level decreases 53a,b,c are each associated with a successively smaller rate of change, with 53a being the relatively largest rate of change and 53c being the relatively smallest rate of change.

Thus, where the user's threshold response level 54 is only slowly increasing (i.e., at lower frequencies; the left-hand portion of the graph of FIG. 5), the rates of change 52a, 53a up or down of the audio tone stimulus level are still relatively constant, as in the standard Bekesy paradigm. However, where the user's threshold levels are predicted, or detected, to be increasing more rapidly (e.g. around the cut-off frequency 46), the respective rates of change of increasing and decreasing audio tone stimulus levels diverge. Rates of change for increasing levels 52b, 52c (after button releases) are steeper; rates of change for decreasing levels 53b, 53c (after button presses) are flatter or slower, and steered towards the expected response curve 54. Through this modification, it is possible to generate more regular and consistent user data from the hearing test. In this particular example, when the actual threshold trace follows the expected threshold trace, the user is able to continue to interact and generate regular data points beyond the previous final data point 45, thereby allowing validation of the user response curve 54 beyond the previous limit imposed by cut-off frequency 46.

Figure 6:
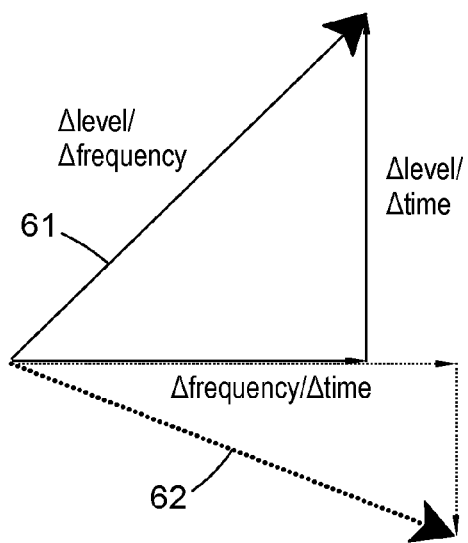
FIG. 6 illustrates differing rates of change for stimulus level vs. frequency and frequency vs. time for a sweeping auditory threshold test.

FIG. 6 illustrates an example of adaptive parameters (in this example, audio stimulus level 61 and audio tone frequency 62) being varied at different rates. In the above discussion of FIG. 5, the rates of change of audio tone stimulus level were varied while increasing or decreasing the level, but frequency was varied in a constant manner. However, in some embodiments, the rates of change of frequency may be varied for specific stimulus levels instead, or the rates of change for both the audio tone level parameter and the audio tone frequency parameter may be varied.

Note also that, if the measured levels of an adaptive parameter are expected to drop off steeply with changes in a second parameter, then rather than increasing the rate of change of the parameter upwards and decreasing the rate of change downwards (c.f. FIG. 5), it may be necessary to follow the opposite procedure—i.e. to increase the rate of change downwards and decrease the rate of change upwards.

It is also possible to adjust the rates of variation or sweep of any of the parameters during tests to obtain data meeting a desired quality criterion. For example, such a criterion could be a minimum total number of user interactions (i.e. data points). Thus, for example, a test may be performed more rapidly for an individual who is fully able, whereas a test may need to be carried out more slowly for users who have some form of physical or cognitive impairment, in order for both tests to generate data meeting one or more same/similar desired quality criterion. For example, the second parameter value (audio tone frequency) may be changed or swept more slowly or more rapidly, depending on the rate and regularity of user interactions, in order to thereby obtain at least a predetermined number of user interactions over the range of values of the second variable parameter of the audio tone stimulus (e.g. a minimum total number necessary to fully validate a user's response curve).

Various audiometric tests may benefit from using modified Bekesy tracking in accordance with one or more aspects of the present disclosure. For example, such audiometric tests include, but are not limited to, Psychometric Tuning Curve (PTC) tests. Other such audiometric tests include, but are not limited to, supra-threshold tests, temporal fine structure tests, masked threshold tests and temporal masking curve tests.

A PTC test may typically be performed for audio and/or signal tones between frequencies of 125 Hz and 16 kHz, in some embodiments between frequencies of 250 Hz and 8 kHz, and in some embodiments preferably between frequencies of 500 Hz and 4 kHz. A PTC test may be performed at any audio/signal tone level above the user's hearing threshold (i.e. any level above 0 dB SL), in some embodiments at signal levels between 10 dB SL and 60 dB SL, and in some embodiments preferably at signal levels between 20 dB SL and 40 dB SL, with a masking signal applied to sweep in a predefined range around each signal tone frequency, particularly from 50% of the signal tone frequency to 150% of the signal tone frequency.

In some embodiments, the masking signal can be applied to sweep around each signal tone frequency in a range of 60% of the signal tone frequency to 140% of the signal tone frequency, particularly between 80% of the signal tone frequency to 120% of the signal tone frequency.

The signal level of the masking signal is continuously modulated according to a user's responses to the audio/stimulus tone of the PTC test. For example, if the user indicates that he can detect the signal tone, then the masker signal level is increased; if the user indicates that he cannot detect the signal tone, then the masker signal level is decreased. A similar approach can be used for the masked threshold (MT) test, which uses an inverted PTC paradigm in which a narrow band of noise with a center frequency is held at a constant frequency while a probe tone sweeps around each noise band.

In a calibrated system, more reliable data can be obtained by modulating the masker intensity (i.e. the signal level of the masking signal) around a curve that would provide a constant output in dB HL. This is so that the user does not experience any jumps in intensity due to discontinuities in the frequency response of the hardware setup, or due to differences in human sensitivity to tones of different frequency.

In an uncalibrated audio system however (assuming the output of the audio system is at least reasonably flat across frequency), and particularly given that the precise output level at each frequency is unknown in an un-calibrated system as explained above. For example, International Patent Application PCT/EP2017/076679 (filed Oct. 19 2017 and herein incorporated by reference in its entirety) discloses that it is advantageous if the masker intensity is modulated relative to a standard weighting curve, such as for example A-weighting, such as defined in IEC 61672:2003, or an equal loudness contour, such as defined in IS0226. This provides a consistent feel of control of the masker intensity to the user across the frequency range of the test and yields more reliable results. It will be readily apparent that modified Bekesy tracking in accordance with the methods of the invention may also enhance such test results.

A temporal masking curve test involves a forward-masking task whereby the masker level required to mask a fixed, low-level pure-tone probe is measured as a function of the masker-probe interval to produce a temporal masking curve. Limiting the probe to a low level minimizes spread of excitation along the basilar membrane and effects of off-frequency listening. As the probe level is fixed, the required masker level increases with increasing masker-probe interval, resulting in temporal masking curves that have positive slopes. For an off-frequency masker, which is assumed to be processed linearly, the temporal masking curve is assumed to reflect decay of masking. As the masker-probe interval is increased, the masker level required at masked threshold increases to compensate for the time course of decay. For an on-frequency masker, the temporal masking curve is assumed to reflect the combined effects of the decay of masking and compression applied to the masker. Therefore, a larger change in masker level would be required to produce a given change in basilar membrane excitation when the response to the masker is compressive. This would be reflected as a steeper on-frequency temporal masking curve compared to an off-frequency temporal masking curve. Assuming the time course of decay of the masker is identical for all masker frequencies (and levels), the degree of basilar membrane compression can be estimated by comparing the slope of a temporal masking curve for an on-frequency masker against the slope of a temporal masking curve for a masker that is processed linearly by the basilar membrane (i.e. off-frequency masker or linear-reference temporal masking curve). Basilar membrane responses can be inferred by plotting the off-frequency masker level against the on-frequency masker level required for each masker-probe interval.

Where the present disclosure is applied to an audiometric test that is a temporal masking curve test (rather than the PTC test described above), the rate of change of the masker level and the masker-probe interval could be varied as the adaptive parameters of the stimulus.

Although the description with reference to FIG. 6, above, is exemplified using potential adaptive parameters of audio stimulus level 61 and audio tone frequency 62, it is appreciated that the test is applicable to any psychophysical test in which a threshold in sensory perception of a first factor is determined while second and third factors are changing over time.

For example, visual tests such as contrast sensitivity tests would be equally applicable. In a test of this nature, the ability to distinguish two lines as distinct objects with varying color and/or intensity can be tested. In this case the adaptive parameters of the stimulus could be the hue (i.e. the frequency) of the line and the distance between the lines. As another option this test could use, as adaptive parameters, the intensity (typically measured in lumens) of the lines and the distance between the lines. Alternatively, or additionally, the ability to read text of varying color and intensity against a specific background could be tested. In this case the adaptive parameters of the stimulus could be the text hue and the background hue. As another option this test could use, as adaptive parameters, the text intensity and the background intensity. In a similar manner to that described above with reference to the auditory example of FIG. 6, the user response can be steered towards the predicted or expected response contour of the user, i.e. the user presses a button when he sees the distinct objects and releases the button when he can no longer see the distinct objects, while color and intensity are varied over time. Further examples may include, but are not limited to visual acuity, where the object size and focus length are variables; peripheral vision, where the object size and angle from central vision are variables; color vision, where the color and intensity of two light sources are varied to match a third source; and taste or smell where the presence of a first smell or taste is tested using the variables of concentration and location.

Figure 7:
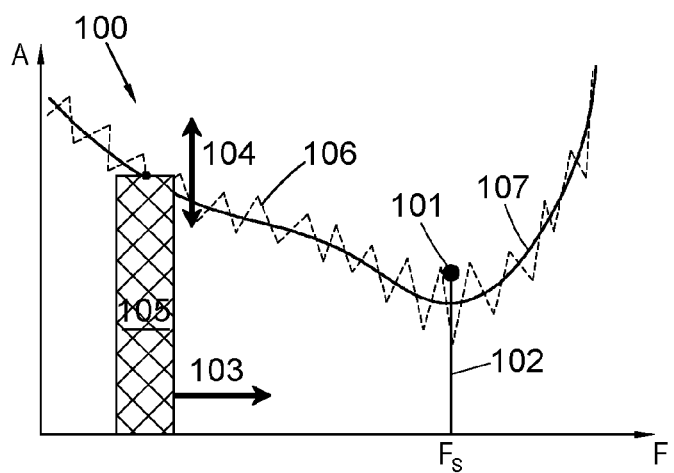
FIG. 7 illustrates Psychometric Tuning Curve (PTC) test results for changes in stimulus level and frequency with adaptive variation of a masker signal.

FIG. 7 illustrates a PTC audiometric test measurement 100. The diagram shows the audio level or intensity A in arbitrary units on the vertical-axis, against audio frequency F on the horizontal-axis. As illustrated, a signal tone 102 at a first sound level 101 is masked by a masker signal 105 particularly sweeping 103 through different frequencies in the proximity of the signal tone 102. The test user indicates at which sound level he hears the signal tone over the masker signal. The signal tone and the masker signal are well within the user's hearing range.

While a signal tone 102 of a constant frequency and intensity 101 is played to the user, a masker signal 105 slowly sweeps 103 from a frequency lower to a frequency higher than the signal tone 102. The rate of sweeping 103 may be constant or may be varied in response to the consistency of the user's interactions. The goal for the user is to hear the signal tone 102. When the user can no longer hear the signal tone 102 (e.g. as indicated by the user by releasing a pushbutton) the masker signal intensity is reduced 104 to a point where the user starts hearing the signal tone 102 (indicated by the user by pressing the pushbutton). While the masker signal tone 105 is still sweeping 103 upwards in frequency, the intensity of the masker signal 105 is increased 104 again, until the user no longer hears the signal tone 102 again. This way, the masker signal intensity oscillates 106 around the user's expected or predicted hearing level response curve 107 (as indicated by the solid line). This hearing level response curve 107 can be compared with a well-established and well-known response curve for people having no hearing loss. Any deviations from this known curve would be indicative of a hearing loss.

In some embodiments, it is desirable that the initial and/or expected user response curves and profiles for changes in one parameter over a range of variation of a second parameter should be predicted with sufficient accuracy to facilitate substantially neutral user interaction across a desired test range. For audiometric purposes, or for example, for threshold curves in Pure Tone Threshold tests, supra-threshold tests (e.g. Psychometric Tuning Curve tests), or equal loudness contour tests, such predictions may be based on information of various types, such as:

ISO7029: Acoustics—Statistical distribution of hearing thresholds as a function of age;
IS0226: Acoustics—Normal equal loudness contours;
prior test results (and particularly confirmed clinical-standard pure tone audiometry) from cohorts of other patients with similar characteristics;
Other available meta-information about the data sets, including:
Reaction times
Estimated accuracy of data set
Time of day
Geographic location
Test duration
Number of interruptions
Demographic user information
Socio-demographic factors, such as:
age of the user
sex of the user
the cognitive capacity of the user
genetic disposition of the user, possibly affecting hearing ability
genomic information for the user
working environment
leisure activities
music listening habits (types, loudness, frequency)
telephone setting preferences (loudness)
chronic or acute illnesses, pathologies affecting hearing ability
prescription/recreational drug use (including alcohol)
Performance details for the user's audio equipment (e.g. mobile audio device and headphones)

A computer program, or mobile device application ("App") comprising computer program code, may be provided to allow a user to self-administer tests using the methods according the invention, when the computer program is loaded, streamed or executed on a personal computer or mobile device.

Figure 8:
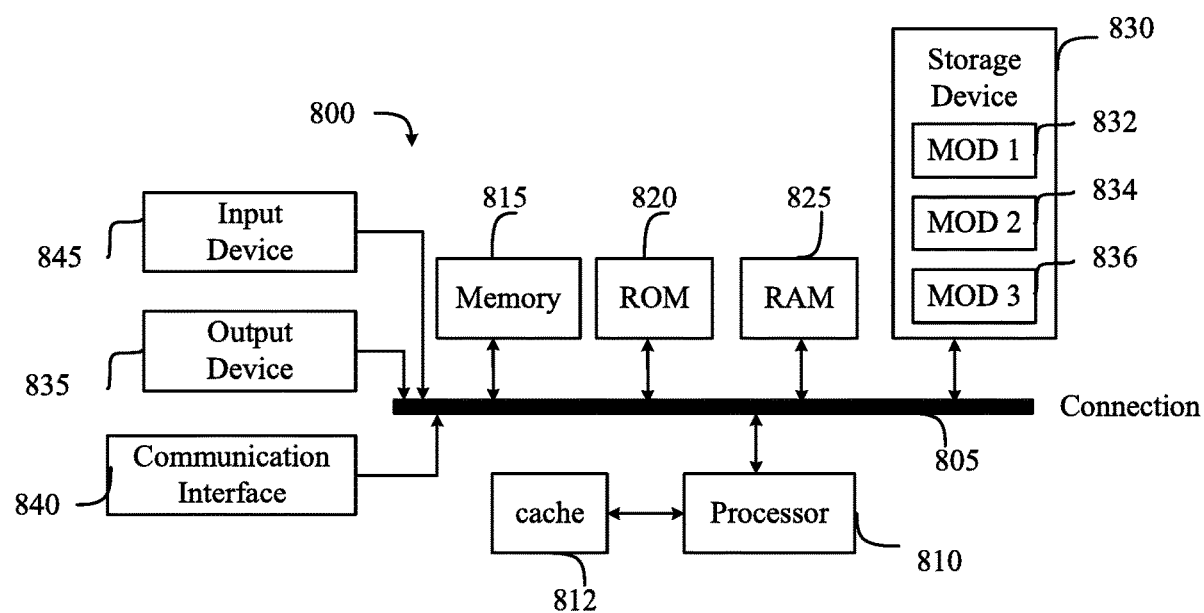
FIG. 8 illustrates an example system for implementing one or more aspects of the present disclosure.

FIG. 8 illustrates an example system embodiment in which various aspects of the present disclosure can be implemented. Persons of ordinary skill in the art will also readily appreciate that other system embodiments are possible. Depicted is a system bus computing system architecture 800 wherein the components of the system are in electrical communication with each other using a bus 805. Exemplary system 800 includes a processing unit (CPU or processor) 810 and a system bus 805 that couples various system components including the system memory 815, such as read only memory (ROM) 820 and random access memory (RAM) 825, to the processor 810. The system 800 can include a cache of high-speed memory connected directly with, in close proximity to, or integrated as part of the processor 810. The system 800 can copy data from the memory 815 and/or the storage device 830 to the cache 812 for quick access by the processor 810. In this way, the cache can provide a performance boost that avoids processor 810 delays while waiting for data. These and other modules can control or be configured to control the processor 810 to perform various actions. Other system memory 815 may be available for use as well. The memory 815 can include multiple different types of memory with different performance characteristics. The processor 810 can include any general-purpose processor and a hardware module or software module, such as module 1 832, module 2 834, and module 3 836 stored in storage device 830, configured to control the processor 810 as well as a special-purpose processor where software instructions are incorporated into the actual processor design. The processor 810 may essentially be a completely self-contained computing system, containing multiple cores or processors, a bus, memory controller, cache, etc. A multi-core processor may be symmetric or asymmetric.

To enable user interaction with the computing device 800, an input device 845 can represent any number of input mechanisms, such as a microphone for speech, a touch-sensitive screen for gesture or graphical input, keyboard, mouse, motion input, speech and so forth. An output device 835 can also be one or more of a number of output mechanisms known to those of skill in the art. In some instances, multimodal systems can enable a user to provide multiple types of input to communicate with the computing device 800. The communications interface 840 can generally govern and manage the user input and system output. There is no restriction on operating on any particular hardware arrangement and therefore the basic features here may easily be substituted for improved hardware or firmware arrangements as they are developed.

Storage device 830 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 825, read only memory (ROM) 820, and hybrids thereof.

The storage device 830 can include software modules 832, 834, 836 for controlling the processor 810. Other hardware or software modules are contemplated. The storage device 830 can be connected to the system bus 805. In one aspect, a hardware module that performs a particular function can include the software component stored in a computer-readable medium in connection with the necessary hardware components, such as the processor 810, bus 805, display 835, and so forth, to carry out the function.

It will further be appreciated by those skilled in the art that although the invention has been described by way of example with reference to several embodiments it is not limited to the disclosed embodiments and that alternative embodiments could be constructed without departing from the scope of the invention as defined in the appended claims.

The presented technology offers a novel and convenient way to provide added clarity to the telephonic communications of receivers who may suffer from known or undiagnosed hearing deficiencies by seamlessly personalizing phone calls. h is to be understood that the present disclosure contemplates numerous variations, options, and alternatives. For clarity of explanation, in some instances the present technology may be presented as including individual functional blocks including functional blocks comprising devices, device components, steps or routines in a method embodied in software, or combinations of hardware and software.

Methods according to the above-described examples can be implemented using computer-executable instructions that are stored or otherwise available from computer readable media. Such instructions can comprise, for example, instructions and data which cause or otherwise configure a general-purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example. The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed is:

1. A method comprising:
generating a user stimulus signal according to a first adaptive parameter and a second adaptive parameter;
modifying the first adaptive parameter in order to generate a plurality of successive variations in the user stimulus signal, such that the plurality of successive variations in the user stimulus signal are generated over one or more given ranges of values of the second adaptive parameter;
receiving, in response to modifying the first adaptive parameter, a plurality of user responses from a given user, each user response indicating that a corresponding one of the plurality of successive variations in the user stimulus signal has occurred; and
based at least in part on an expected user response curve for the given user and a calculated time interval between successive ones of the plurality of user responses received from the given user, adjusting an instantaneous rate of change for modifying the first adaptive parameter such that the user responses are steered toward a neutral state around the expected user response curve, wherein the instantaneous rate of change for modifying the first adaptive parameter is increased in response to determining that one or more of the plurality of user responses will not reach the neutral state around the expected user response curve.

2. The method of claim 1, wherein:
the user stimulus signal is an audio signal;
the first adaptive parameter is an amplitude or level of the audio signal; and
the second adaptive parameter is a frequency of the audio signal.

3. The method of claim 2, wherein the generated plurality of successive variations in the user stimulus signal are used to perform one or more of an audiometric test, a supra-threshold test, a psychometric tuning curve test, a masked threshold test, a temporal fine structure test, and a temporal masking curve test.

4. The method of claim 3, wherein:
the supra-threshold test is a psychometric tuning curve (PTC) test;
the PTC test is measured for user stimulus signal tones between frequencies of 500 Hz and 4 kHz, and at an audible sound level for the user; and
a masking signal for the user stimulus signal sweeps from 50% of the user stimulus signal tone frequency to 150% of the user stimulus signal tone frequency.

5. The method of claim 1, further comprising modifying the expected user response curve for the given user in response to determining that the plurality of user responses do not exhibit a neutral state around an expected user response curve.

6. The method of claim 5, wherein the instantaneous rate of change for modifying the first adaptive parameter is decreased in response to determining that one or more of the plurality of user responses have exceeded the neutral state around the expected user response curve.

7. The method of claim 5, wherein:
the neutral state around the expected user response curve comprises an equal time interval between successive ones of the received plurality of user responses; and
the instantaneous rate of change for modifying the first adaptive parameter is adjusted until the equal time interval between successive ones of the received plurality of user responses is obtained.

8. The method of claim 5, wherein the second adaptive parameter is continuously varied in order to steer the plurality of user responses towards the neutral state around the expected user response curve.

9. The method of claim 5, wherein modifying the expected user response curve for the given user comprises continually adjusting the expected response curve to maximize a probability of obtaining the neutral state.

10. The method of claim 1, wherein the second adaptive parameter is continuously varied monotonically across the one or more given ranges of values.

11. An auditory testing device comprising:
at least one processor; and
at least one memory storing instructions, which when executed cause the at least one processor to:
generate a user stimulus signal according to a first adaptive parameter and a second adaptive parameter;
modify the first adaptive parameter in order to generate a plurality of successive variations in the user stimulus signal, such that the plurality of successive variations in the user stimulus signal are generated over one or more given ranges of values of the second adaptive parameter;
receive, in response to modifying the first adaptive parameter, a plurality of user responses from a given user, each user response indicating that a corresponding one of the plurality of successive variations in the user stimulus signal has occurred; and based at least in part on an expected user response curve for the given user and a calculated time interval between successive ones of the plurality of user responses received from the given user, adjust an instantaneous rate of change for modifying the first adaptive parameter such that the user responses are steered toward a neutral state around the expected user response curve, wherein the instantaneous rate of change for modifying the first adaptive parameter is increased in response to determining that one or more of the plurality of user responses will not reach the neutral state around the expected user response curve.

12. The auditory testing device of claim 11, wherein:
the user stimulus signal is an audio signal;
the first adaptive parameter is an amplitude or level of the audio signal; and
the second adaptive parameter is a frequency of the audio signal.

13. The auditory testing device of claim 12, wherein the generated plurality of successive variations in the user stimulus signal are used to perform one or more of an audiometric test, a supra-threshold test, a psychometric tuning curve test, a temporal fine structure test, and a temporal masking curve test.

14. The auditory testing device of claim 13, wherein:
the supra-threshold test is a psychometric tuning curve (PTC) test;
the PTC test is measured for user stimulus signal tones between frequencies of 500 Hz and 4 kHz, and at an audible sound level for the user; and
a masking signal for the user stimulus signal sweeps from 50% of the user stimulus signal tone frequency to 150% of the user stimulus signal tone frequency.

15. The auditory testing device of claim 11, wherein the instructions further cause the processor to modify the expected user response curve for the given user in response to determining that the plurality of user responses do not exhibit a neutral state around an expected user response curve.

16. The auditory testing device of claim 15, wherein the instantaneous rate of change for modifying the first adaptive parameter is decreased in response to determining that one or more of the plurality of user responses have exceeded the neutral state around the expected user response curve.

17. The auditory testing device of claim 15, wherein:
the neutral state around the expected user response curve comprises an equal time interval between successive ones of the received plurality of user responses; and
the instantaneous rate of change for modifying the first adaptive parameter is adjusted until the equal time interval between successive ones of the received plurality of user responses is obtained.

18. The auditory testing device of claim 15, wherein the second adaptive parameter is continuously varied in order to steer the plurality of user responses towards the neutral state around the expected user response curve.

19. The method of claim 15, wherein the instructions cause the processor to modify the expected user response curve for the given user by continually adjusting the expected response curve to maximize a probability of obtaining the neutral state.

20. The auditory testing device of claim 11, wherein the second adaptive parameter is continuously varied monotonically across the one or more given ranges of values.

* * * * *